(12) United States Patent
Flores

(10) Patent No.: US 7,645,228 B2
(45) Date of Patent: Jan. 12, 2010

(54) SEXUAL ENHANCEMENT DEVICE

(76) Inventor: Samuel O. Flores, 13333 Thunderhead St., San Diego, CA (US) 92129-2329

( * ) Notice: Subject to any disclaimer, the term of this patent is extended or adjusted under 35 U.S.C. 154(b) by 1161 days.

(21) Appl. No.: 11/022,413

(22) Filed: Dec. 23, 2004

(65) Prior Publication Data

US 2006/0142638 A1    Jun. 29, 2006

(51) Int. Cl.
*A61F 5/00* (2006.01)
(52) U.S. Cl. ........................................ 600/38
(58) Field of Classification Search .............. 600/38–41
See application file for complete search history.

(56) References Cited

U.S. PATENT DOCUMENTS

| 879,534 | A | 2/1908 | Fraser | |
|---|---|---|---|---|
| 997,067 | A | 7/1911 | Lang | |
| 3,926,184 | A | 12/1975 | Gehl | 128/79 |
| 4,381,000 | A | 4/1983 | Duncan | 128/79 |
| 4,440,183 | A | 4/1984 | Miller | 128/79 |
| 4,643,175 | A | 2/1987 | Chapman | 128/79 |
| 5,218,974 | A | 6/1993 | Garrett | 128/845 |
| 5,244,454 | A | 9/1993 | Coates | 600/41 |
| 5,728,043 | A | 3/1998 | Yong | 600/39 |
| 5,893,827 | A | 4/1999 | Jaquez | 600/38 |
| 5,928,134 | A | 7/1999 | Vergara | 600/38 |
| 6,123,664 | A | 9/2000 | Ard | 600/38 |
| 6,579,229 | B1 | 6/2003 | Nan | 600/38 |

*Primary Examiner*—John P Lacyk
(74) *Attorney, Agent, or Firm*—John R. Ross; John R. Ross, III

(57) ABSTRACT

A sexual enhancement device for improving a user's sexual experience. A prostate pad is positioned adjacent to a male user's perineum below his prostate gland. A first prostate strap is connected to the prostate pad and is looped behind the user's neck. When the prostate strap is tightened, the prostate pad applies pressure to the perineum. This pressure is felt at the user's prostate and provides pleasurable stimulation to the prostate. A second prostate strap is also connected to the prostate pad and is looped around the user's waist. Preferably, the second prostate strap is also looped over the top of the user's erect penis. When looped over the top of the penis, tightening of the second prostate strap assists in restricting the flow of blood out of the erect penis, preferably allowing for an erection that lasts longer than it would otherwise. In a preferred embodiment, the pressure applied by the prostate pad can be dynamically increased or decreased by the user leaning his neck backwards or forwards, and also by the user arching his back and thrusting his hips. Also, in a preferred embodiment the tightness of the second prostate strap can be adjusted without having to interrupt sexual activity.

17 Claims, 7 Drawing Sheets

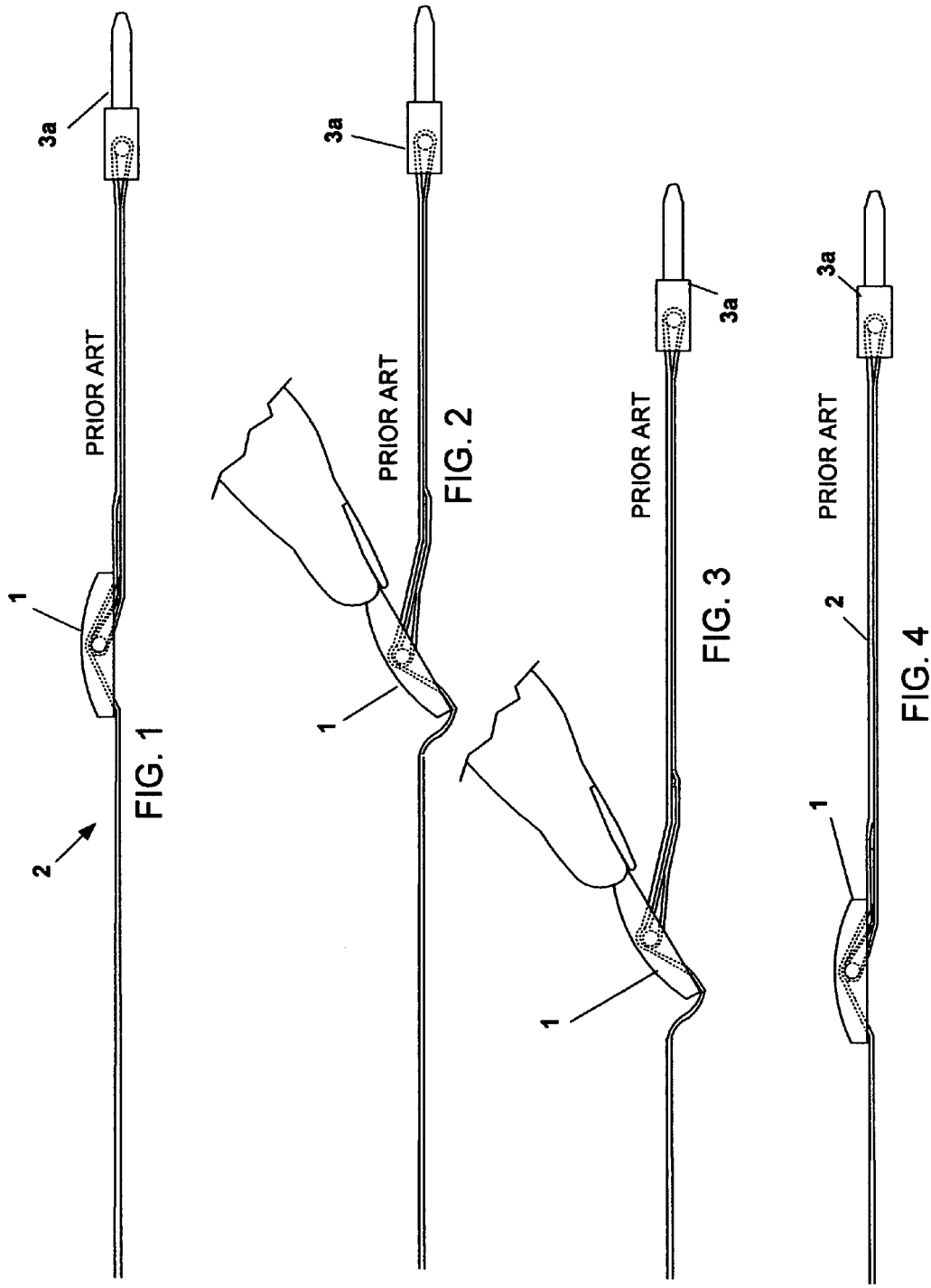

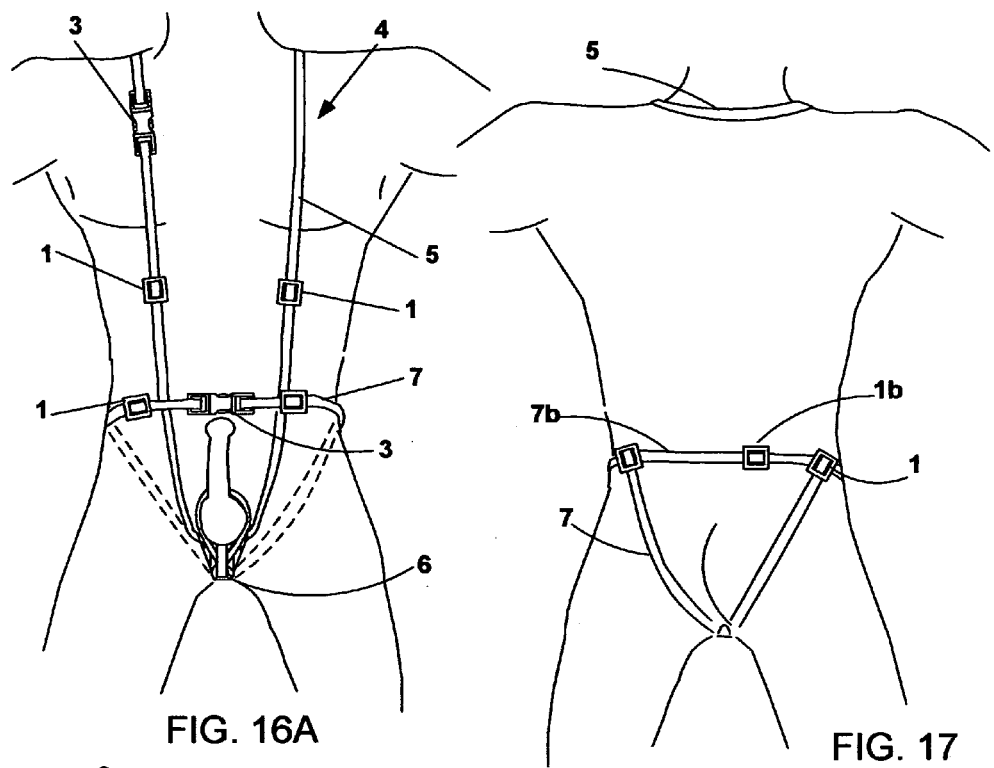
FIG. 16A
FIG. 17
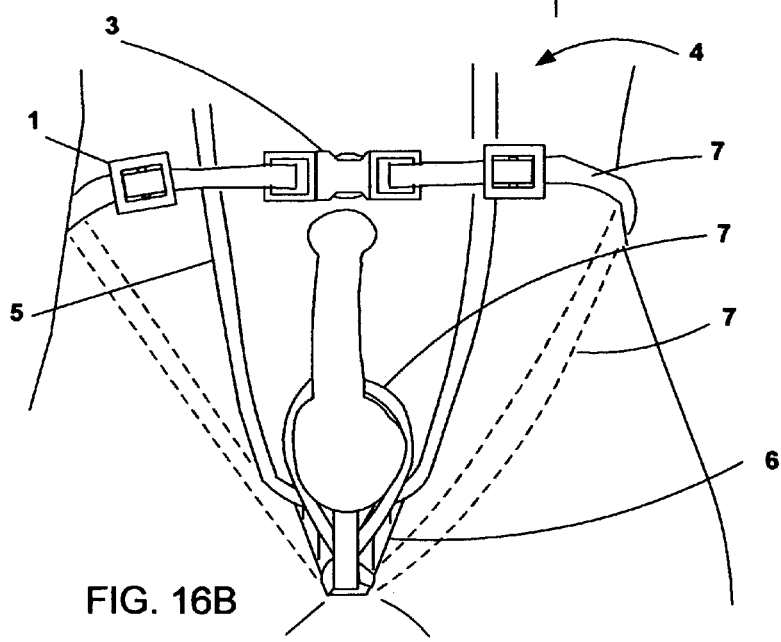
FIG. 16B

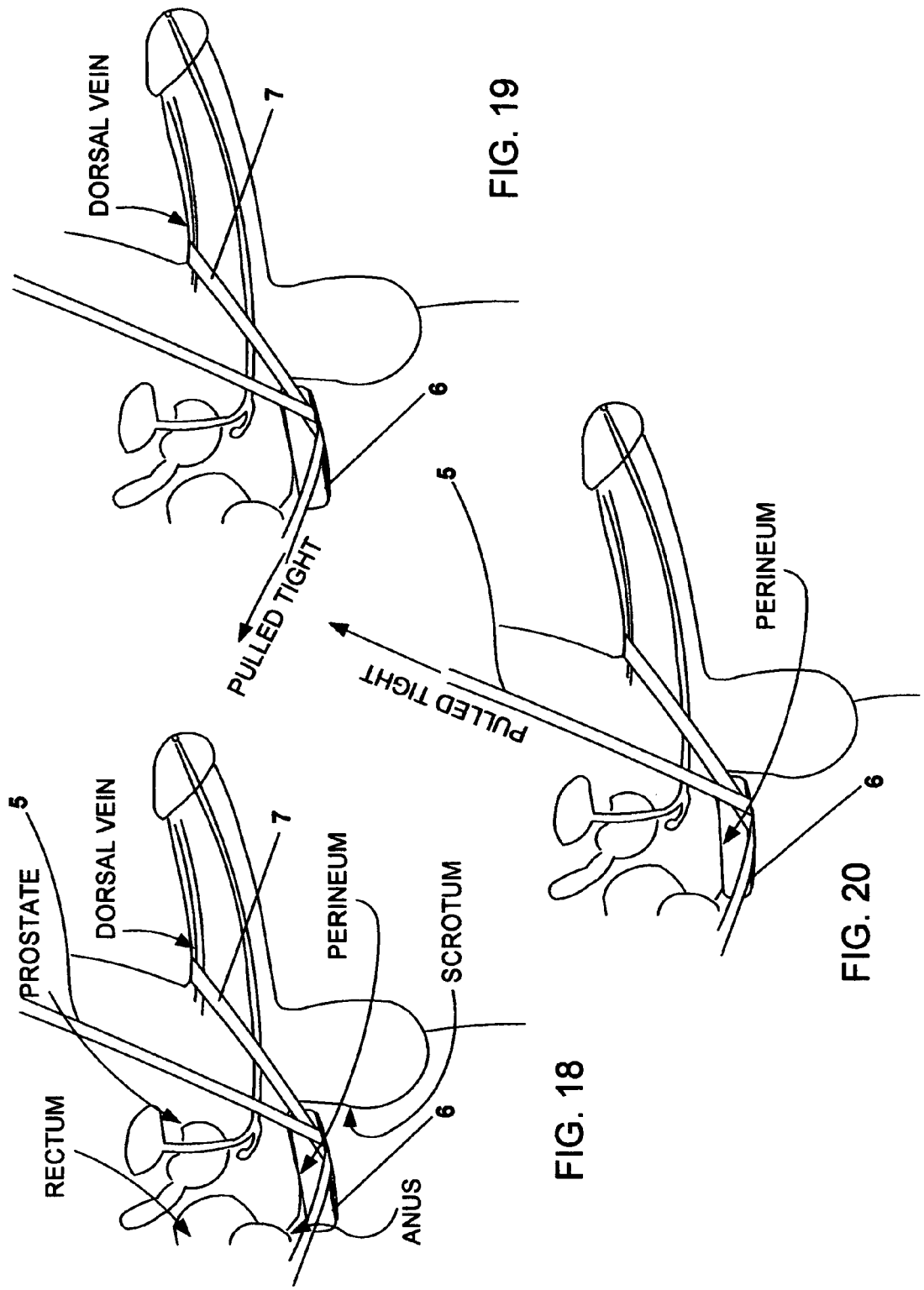

SEXUAL ENHANCEMENT DEVICE

BACKGROUND OF THE INVENTION

Sexual intercourse is a basic human need for both men and women. A majority of men are able to achieve and maintain an erection and are able to complete successful sexual intercourse. Nevertheless, many men are interested in enhancing and improving their sex lives. They may utilize sexual devices while having sex to enhance their arousal and intensify their sensations.

The Prostate and the Perineum

The prostate is a small gland, about the size and shape of a quail's egg that is nestled in the man's pubic bone and surrounded by the pelvic muscles. The main function of the prostate is reproduction. The testicles produce sperm that fertilize eggs. The vas deferens carries this sperm to the prostate, where it mixes with fluid from the prostate and seminal vesicles. When a male experiences orgasm, he ejaculates this fluid, which is comprised of 5% sperm and 95% seminal/prostate fluid.

The prostate is a nerve-rich organ that is extremely sensitive. So, stimulating the prostate has been known to intensify a male's orgasm. The easiest way to stimulate the prostate gland is by applying external pressure to the perineum. The perineum is a hairless patch of skin located at the base of the scrotum. When the perineum is massaged externally the prostate is indirectly stimulated.

Penis Dorsal Vein

The penis dorsal vein is the main draining vein for blood in an engorged penis. By restricting the flow of blood out of the penis through the dorsal vein, an erect penis should remain engorged longer. Therefore, a male will be able to retain his erection longer and prolong his sexual activity.

There is a class of devices, called venous flow control devices, that are known to help men who are able to achieve an erection but are not able to maintain it. These are rings, bands, or straps that work by constricting the flow of blood through the dorsal vein on top of the penis.

Constrictor rings (cock rings) have been around for a long time. They can be worn around the circumference of the base of the penis (where they can be uncomfortable and interfere with ejaculation), or looped over the top of the base of the penis and behind the scrotum. There are non-adjustable and adjustable versions. Adjustable versions can be tightened or loosened as the penis engorges. However, they usually require that sexual activity be interrupted while the tightness is adjusted.

Adjustable Strap Buckles

Adjustable strap buckles are known in the prior art. FIGS. 1-4 illustrate how they are utilized to adjust the length of straps.

FIG. 1 shows adjustable strap buckle 1 attached to strap 2. Strap 2 is also looped around male quick release buckle 3a. The looped portion of strap 2 is to the right of adjustable strap buckle 1 and the non-looped portion of strap 2 is to the left of adjustable strap buckle 1.

In FIG. 2, a user has positioned his finger at the side of adjustable strap buckle 1 and has lifted up on adjustable strap buckle 1.

In FIG. 3, the user has moved adjustable strap buckle 1 towards the left approximately two inches. This action has increased the distance from adjustable strap buckle 1 to male quick release buckle 3a by approximately one inch. The overall effect has been to decrease the length of strap 2 by approximately one inch, as shown in FIG. 4.

What is needed is a better device for enhancing and improving the sexual experience.

SUMMARY OF THE INVENTION

The present invention provides a sexual enhancement device for improving a user's sexual experience. A prostate pad is positioned adjacent to a male user's perineum below his prostate gland. A first prostate strap is connected to the prostate pad and is looped behind the user's neck. When the prostate strap is tightened, the prostate pad applies pressure to the perineum. This pressure is felt at the user's prostate and provides pleasurable stimulation to the prostate. A second prostate strap is also connected to the prostate pad and is looped around the user's waist. Preferably, the second prostate strap is also looped over the top of the user's erect penis. When looped over the top of the penis, tightening of the second prostate strap assists in restricting the flow of blood out of the erect penis, preferably allowing for an erection that lasts longer than it would otherwise. In a preferred embodiment, the pressure applied by the prostate pad can be dynamically increased or decreased by the user leaning his neck backwards or forwards, and also by the user arching his back and thrusting his hips. Also, in a preferred embodiment the tightness of the second prostate strap can be adjusted without having to interrupt sexual activity.

BRIEF DESCRIPTION OF THE DRAWINGS

FIGS. 1-4 show a prior art adjustable strap buckle.
FIGS. 16A-23 illustrate the utilization of a preferred embodiment of the present invention.

DETAILED DESCRIPTION OF THE PREFERRED EMBODIMENTS

First Preferred Embodiment

As shown in FIGS. 16A-17, a user has donned sexual enhancement device 4. In the preferred embodiment, sexual enhancement device 4 includes prostate pad 6, first prostate strap 5 and second prostate strap 7. First prostate strap 5 is looped behind the user's neck and is looped through prostate pad 6. Prostate pad 6 is positioned behind the user's testicles and between the user's scrotum and the anus. Second prostate strap 7 is fed through prostate pad 6, and is looped over the top of the user's penis. Both ends of second prostate strap 7 pass between the user's legs, pass in opposite directions around the user's buttocks and are connected just below the user's waist. By tightening second prostate strap 7 over the top of the user's penis, the user is able to restrict the flow of blood from the penis, thereby allowing the user to maintain an erection for a longer period of time. Also, by tightening first prostate strap 5 behind the user's neck, prostate pad 6 exerts upwards pressure on the user's prostate, thereby pleasurably stimulating the user's prostate. In the preferred embodiment, sexual enhancement device 4 is worn by the user during sexual intercourse. By wearing sexual enhancement device 4, the user should be able to increase the amount of time that he is able to maintain an erection and also increase the intensity of his orgasm.

Preferred Prostate Pad

A preferred prostate pad is shown in FIGS. 5-12.

Figure 5:
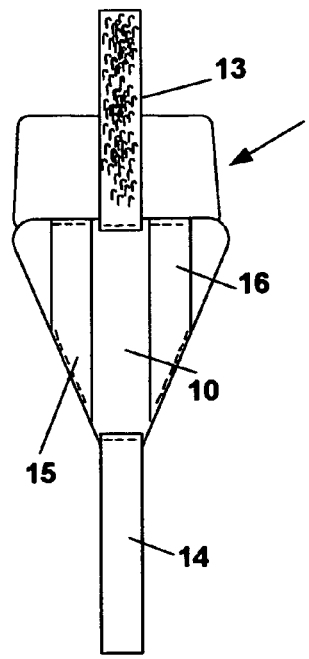
FIGS. 5-12 show a preferred prostate pad.
Figure 6:
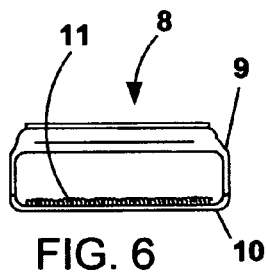
Figure 7:
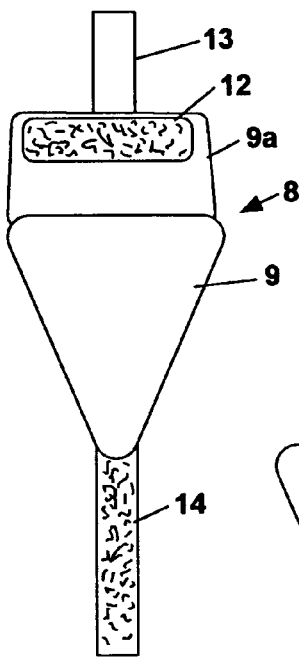

FIG. 5 shows a bottom view of prostate pad cover 8, FIG. 6 shows a side view of prostate pad cover 8 and FIG. 7 shows a top view of prostate pad cover 8.

Cloth upper section 9 is sewn to vinyl lower section 10 (FIG. 6). Velcro® hooks 11 are sewn onto lower section 10. (Velcro® is a registered trademark of Velcro Industries and refers generally to separable fasteners; namely, hook and loop-type fasteners and components thereof.) Upper section 9 includes top portion 9a. Velcro® loops 12 are sewn onto top portion 9a (FIG. 7). Velcro® hook strip 13 and Velcro® loop strip 14 are sewn onto vinyl lower section 10 (FIGS. 5 and 7). Elastic loops 15 and 16 are also sewn onto vinyl lower section 10 (FIG. 5).

Figure 8:
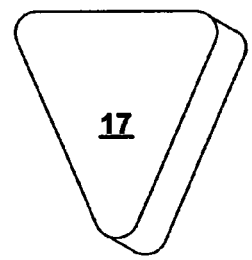

FIG. 8 shows a preferred pad insert 17. Preferably, pad insert 17 is fabricated from ½ inch thick foam.

Figure 9:
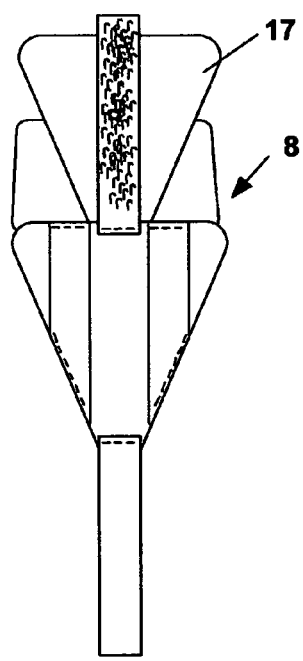

In FIG. 9, pad insert 17 is being inserted into the opening of prostate pad cover 8.

Figure 10:
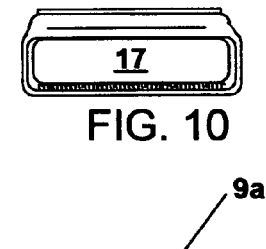

In FIG. 10, pad insert 17 has been fully inserted into prostate pad cover 8.

Figure 11:

In FIG. 11, top portion 9a has been folded over pad insert 17 and secured by fastening Velcro® loops 12 (FIG. 7) to Velcro® hooks 11 (FIG. 6).

Figure 12:
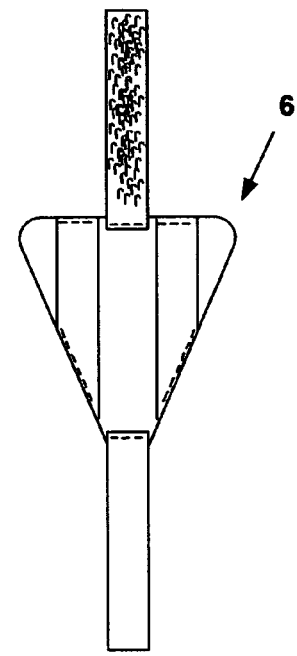

FIG. 12 shows a bottom view of preferred prostate pad 6 with foam pad insert 17 (FIG. 8) secured inside.

Preferred Sexual Enhancement Device

Figure 13:
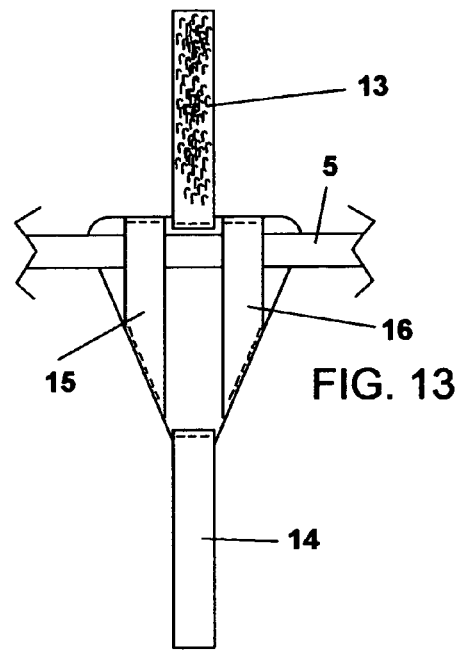
FIGS. 13-15 show a preferred sexual enhancement device.
Figure 14:
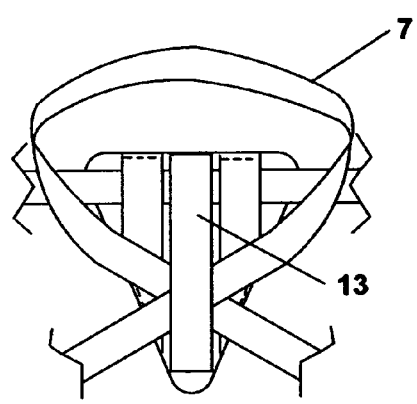
Figure 15:
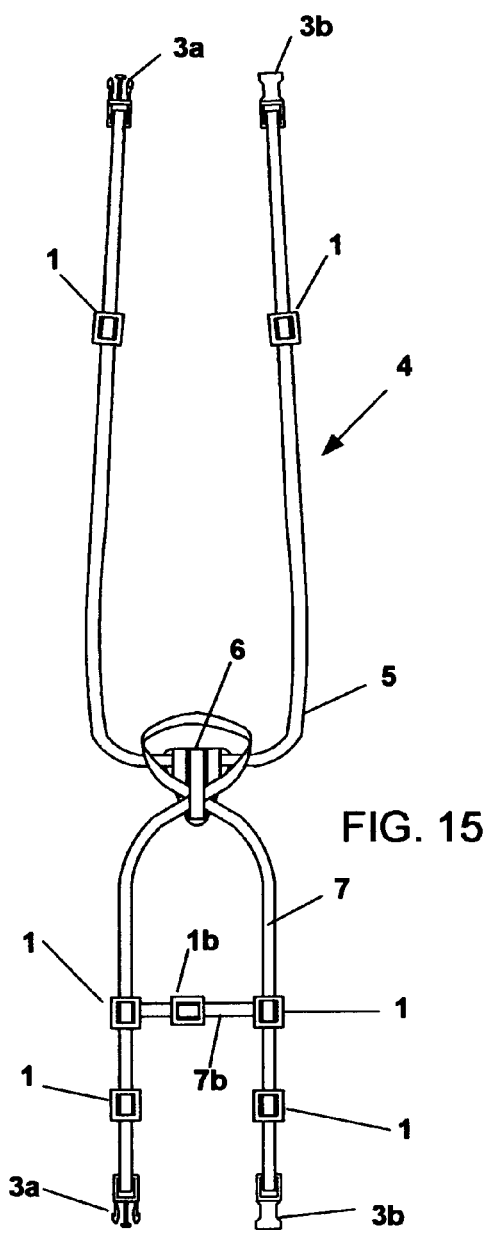

Preferred sexual enhancement device 4 is shown in FIGS. 13-15. Preferred sexual enhancement device 4 includes prostate pad 6, vinyl first prostate strap 5 and vinyl second prostate strap 7.

In FIG. 13, first prostate strap 5 has been looped through elastic loops 15 and 16.

In FIG. 14, second prostate strap 7 has been looped through the loop formed by fastening Velcro® hook strip 13 to Velcro® loop strip 14.

FIG. 15 shows preferred sexual enhancement device 4. First prostate strap 5 includes adjustable strap buckles 1 and male quick release buckle section 3a and female quick release buckle section 3b. Second prostate strap 7 also includes adjustable strap buckles 1 and male quick release buckle section 3a and female quick release buckle section 3b. Preferably, second prostate strap 7 also includes waist size adjustment section 7b and adjustable strap buckle 1b. The length of waist size adjustment section 7b can be adjusted by utilizing adjustable strap buckle 1b.

Preferred Method for Donning and Utilizing the Sexual Enhancement Device

In FIGS. 16A-17, a user is shown after having donned sexual enhancement device 4. As explained above, first prostate strap 5 is looped behind the user's neck and is looped through prostate pad 6. Prostate pad 6 is positioned between the user's scrotum and the user's anus. Second prostate strap 7 is looped around the user's waist, is fed through prostate pad 6, and is looped over the top of the user's penis. Male quick release buckle sections 3a and female quick release buckle sections 3b (FIG. 15) are connected to form quick release buckles 3. Sexual enhancement device 4 can be easily adjusted to accommodate a variety of body sizes by adjusting adjustable strap buckles 1. As explained above, adjustable strap buckles 1 are easily adjusted (FIGS. 1-4) so that they can be manipulated by the user even while engaged in sexual activity.

By tightening second prostate strap 7 over the top of the user's penis, the user is able to restrict the flow of blood from the penis, thereby allowing the user to maintain an erection for a longer period of time. Second prostate strap 7 is preferably tightened by manipulating adjustable strap buckles 1. This can be done even while the user is engaged in sexual activity. Also, by tightening first prostate strap 5 behind the user's neck, prostate pad 6 exerts upwards pressure on the user's prostate, thereby pleasurably stimulating the user's prostate. Furthermore, as explained below, the user can dynamically increase or decrease the pressure on his prostate merely by moving his neck backward and forward without interrupting sexual activity.

A more detailed explanation of the utilization of sexual enhancement device 4 can be seen by referring to FIGS. 18-23.

FIGS. 18-20 show a detailed side view of first prostate strap 5, second prostate strap 7 and prostate pad 6. Also, depicted are a user's erect penis, the rectum, the anus, the prostate gland, the perineum, the scrotum and the dorsal vein in the erect penis.

In FIG. 18, sexual enhancement device 4 has been donned by the user in the fashion depicted in FIGS. 16A-17. It should be noted that prostate pad 6 is positioned adjacent to the perineum below the prostate.

In FIG. 19, the user has tightened second prostate strap 7. Second prostate strap 7 is preferably tightened by manipulating adjustable strap buckles 1 on strap 7 (FIGS. 16A and 16B). As second prostate strap 7 is tightened, it bears down on the dorsal vein restricting the outward flow of blood from the erect penis. A user with erectile dysfunction problems should now be able to maintain his erection for a longer period of time.

In FIG. 20, the user has tightened first prostate strap 5. First prostate strap 5 is initially tightened by manipulating adjustable strap buckles 1 on strap 5 (FIG. 16A). As first prostate strap 5 is tightened, prostate pad 6 bears upward on the user's perineum. This pressure is felt at the prostate and causes stimulation of the prostate, which in turn gives the user a pleasurable sensation.

Figure 23:
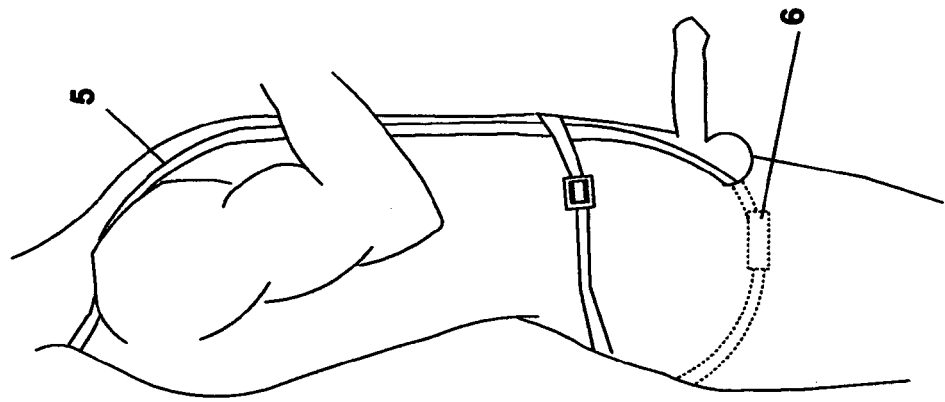
Figure 22:
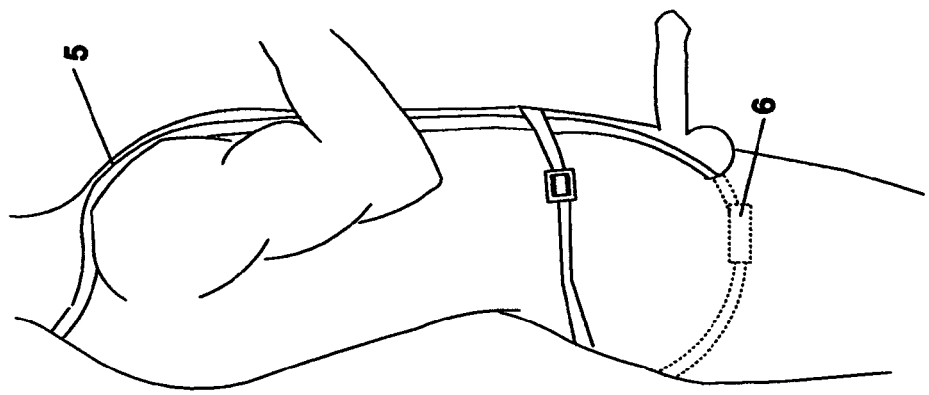
Figure 21:
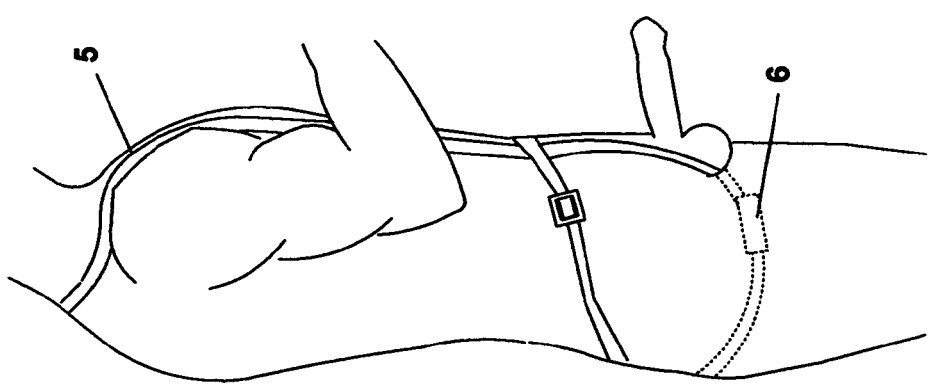

FIGS. 21-23 depict a method by which the user can further tighten and release tension on first prostate strap 5.

In FIG. 21, the user is shown in a relaxed position with his neck bent forward.

In FIG. 22, the user has moved his neck so that it is straightened and has thrust his hips forward and arched his back. This action has caused a further tightening of first prostate strap 5 resulting in increased pressure at the user's prostate.

In FIG. 23, the user has leaned his neck backwards and has raised his shoulders causing even further tightening of first prostate strap 5 and even further pressure at the user's prostate.

The movements depicted in FIGS. 21-23 are similar to the movements naturally made by a male during sexual intercourse. Making these movements will cause pressure on the prostate to increase and then decrease in a rhythmical fashion, thereby pleasurably massaging and stimulating the prostate. It should be noted that during sexual activity the user's movements alone cause the variation of pressure applied by prostate pad 6 and that the user does not have to use his hands to pull tight on strap 5 to adjust the pressure.

Second Preferred Embodiment

Figure 24:
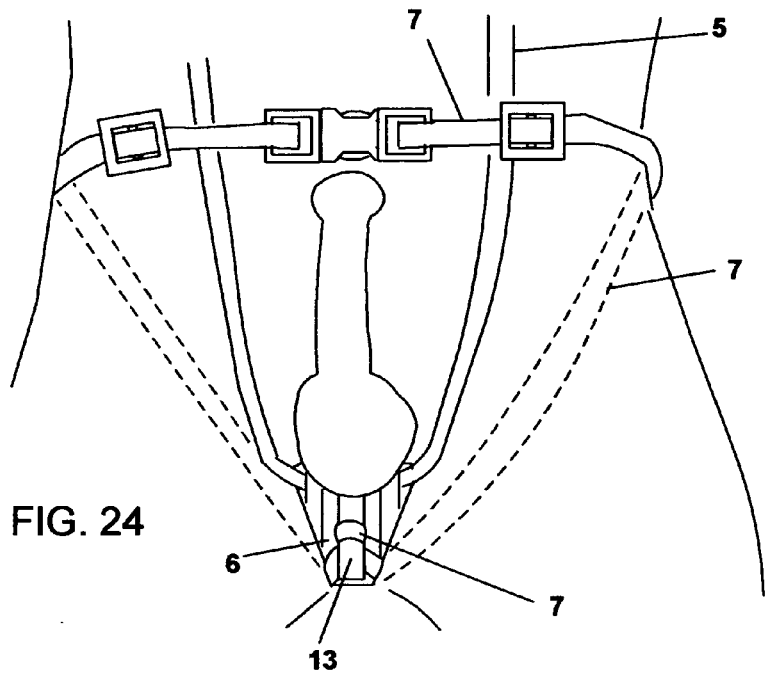
FIG. 24 shows another preferred embodiment of the present invention.

A second preferred embodiment is shown in FIG. 24. The second preferred embodiment recognizes that some users may neither need nor desire the benefits of second prostate strap 7 and instead may only want the stimulation to the prostate gland achieved as a result of first prostate strap 5 and prostate pad 6.

In FIG. 24, the user has removed second prostate strap 7 (FIG. 16B) from his erect penis. Instead second prostate strap 7 is looped around Velcro® hook strip 13 and Velcro® loop strip 14 (Velcro® loop strip 14 shown in FIG. 7) of prostate pad 6 and the user's waist. Second prostate strap 7 assists in holding prostate pad 6 in a position adjacent to the user's perineum and under the user's prostate gland. In this embodiment, the user does not want a strap looped over the top of his penis. Rather, the user only wants prostate pad 6 situated to stimulate his prostate. The user can tighten first prostate strap 5 in a fashion similar to that described above (i.e., by utilizing natural body movements) to increase pressure on his prostate.

Figure 25:
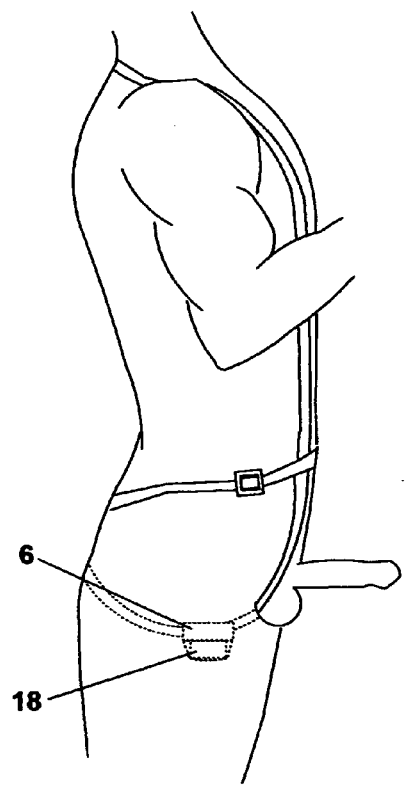
FIG. 25 shows another preferred embodiment of the present invention.

Although the above-preferred embodiments have been described with specificity, persons skilled in this art will recognize that many changes to the specific embodiments disclosed above could be made without departing from the spirit of the invention. For example, although it was stated that the preferred method for using the present invention was during sexual intercourse, the sexual enhancement device 4 could also be used by the wearer while masturbating. Additionally, as shown in FIG. 25, small battery-operated vibrating device 18 can be attached externally to prostate pad 6 to further enhance stimulation. Therefore, the attached claims and their legal equivalents should determine the scope of the invention.

What is claimed is:

1. A sexual enhancement device for improving a user's sexual experience, comprising:
   A) a prostate pad positioned adjacent to said user's perineum below said user's prostate gland,
   B) a first prostate strap connected to said prostate pad and adapted to be looped behind said user's neck,
   C) a second prostate strap connected to said prostate pad and adapted to be looped around said user's waist,
   wherein tightening of said first prostate strap causes said prostate pad to apply pressure to said prostate gland.

2. The sexual enhancement device as in claim 1, wherein said prostate pad comprises:
   A) a foam insert, and
   B) at least one loop for receiving either of said first prostate strap or said second prostate strap.

3. The sexual enhancement device as in claim 1, wherein said second prostate strap is looped over the top of said user's erect penis, wherein tightening of said second prostate strap assists in restricting the flow of blood out of said user's erect penis.

4. The sexual enhancement device as in claim 1, wherein said first prostate strap comprises:
   A) a quick release buckle, and
   B) at least one adjustable strap buckle for adjusting the length of said first prostate strap.

5. The sexual enhancement device as in claim 1, wherein said first prostate strap is tightened as a result of said user's natural movements.

6. The sexual enhancement device as in claim 1, wherein said first prostate strap is tightened as a result of said user moving his neck backwards.

7. The sexual enhancement device as in claim 1, wherein said first prostate strap is tightened as a result of said user arching his back and thrusting his hips.

8. The sexual enhancement device as in claim 1, wherein said pressure applied to said perineum pleasurably stimulates said perineum.

9. The sexual enhancement device as in claim 1, wherein said pressure applied to said perineum is felt at said prostate gland so as to pleasurably stimulate said prostate gland.

10. The sexual enhancement device as in claim 1, wherein said second prostate strap further comprises a waist size adjustment section.

11. The sexual enhancement device as in claim 3, wherein said second prostate strap comprises:
    A) a quick release buckle, and
    B) at least one adjustable strap buckle for adjusting the degree of said tightening of said second prostate strap over the top of said user's erect penis.

12. The sexual enhancement device as in claim 3, wherein said second prostate strap assists in restricting the flow of blood leaving said user's erect penis by bearing down on said user's penis dorsal vein.

13. The sexual device as in claim 1, further comprising an external vibrating device attached to said prostate pad.

14. A sexual enhancement device for improving a user's sexual experience, comprising:
    A) a prostate pad means positioned adjacent to said user's perineum below said user's prostate gland,
    B) a first prostate strap means connected to said prostate pad means and adapted to be looped behind said user's neck,
    C) a second prostate strap means connected to said prostate pad means and adapted to be looped around said user's waist,
    wherein tightening of said first prostate strap means causes said prostate pad means to apply pressure to said prostate gland.

15. The sexual enhancement device as in claim 14, wherein said second prostate strap means is looped over the top of said user's erect penis, wherein tightening of said second prostate strap means assists in restricting the flow of blood out of said user's erect penis.

16. A sexual enhancement device for improving a user's sexual experience, comprising:
    A) a prostate pad,
    B) a first prostate strap attached to said prostate pad, defining two ends with connectors at each end and having a length sufficient with said two ends connected to form a loop, said loop adapted to run up the front of said user's body and behind his neck,
    C) a second prostate strap attached to said prostate pad defining two ends with connectors at each end and having a length sufficient with said two ends connected to form a loop through said user's legs with said ends of said second prostate strap passing in opposite directions around said user's buttocks with said connectors adapted to be connected at the waist region of said user's body,
    wherein with said prostate pad positioned adjacent to said user's perineum and said prostate straps positioned as suggested in B) and C) above, tightening of said first prostate strap by a user causes said prostate pad to apply pressure to said user's prostate gland.

17. The sexual enhancement device as in claim 16, wherein said second prostate strap is looped over the top of said user's penis.

* * * * *